United States Patent [19]

Inahara

[11] Patent Number: 4,688,579
[45] Date of Patent: Aug. 25, 1987

[54] INPUT DEVICE FOR HARD-WIRE PATIENT MONITORING SYSTEM

[75] Inventor: Kazuo Inahara, Kawagoe, Japan

[73] Assignee: Nihon Kohden Corporation, Tokyo, Japan

[21] Appl. No.: 742,603

[22] Filed: Jun. 10, 1985

[30] Foreign Application Priority Data

Jun. 18, 1984 [JP] Japan .................... 59-089521[U]

[51] Int. Cl.⁴ .................................. A61B 5/04
[52] U.S. Cl. ........................................ 128/695
[58] Field of Search ............... 128/630, 690, 695, 696, 128/706, 220, 903

[56] References Cited

U.S. PATENT DOCUMENTS

| | | | |
|---|---|---|---|
| 3,690,313 | 9/1972 | Weppner et al. | 128/696 |
| 3,865,101 | 2/1975 | Saper et al. | 128/696 |
| 3,915,154 | 10/1975 | Cosentino | 128/696 |
| 4,223,683 | 9/1980 | Lown et al. | 128/706 |
| 4,250,888 | 2/1981 | Grosskopf | 128/706 |
| 4,331,962 | 5/1982 | Neumann | 128/212 |

*Primary Examiner*—William E. Kamm
*Attorney, Agent, or Firm*—Hoffmann, Dilworth, Barrese & Baron

[57] ABSTRACT

An input device for supplying detected signals from electrodes and transducers attached to a patient to a patient monitoring system used in an ICU or a CCU includes a case having a plug-in connector for transmission of the signals and power between the input device and the system, and a plurality of lines for receiving physiological input signals, a RAM disposed in the case for storing patient data items necessary for monitoring a patient, a backup battery disposed in the case for backing up the RAM, and a switch disposed in the case and actuatable in response to detachment of the case from the patient monitoring system for switching from a power supply of the patient monitoring system to the backup battery to keep the RAM energized.

3 Claims, 4 Drawing Figures

INPUT DEVICE FOR HARD-WIRE PATIENT MONITORING SYSTEM

BACKGROUND OF THE INVENTION

The present invention relates to an input device for supplying detected signals from electrodes, transducers, etc. attached to a patient to a hard-wire patient monitoring system used in an ICU or a CCU, for example.

When a patient in care of a hard-wire patient monitoring system such as an ICU is to be moved for a certain distance, it is necessary to detach many electrodes and transducers from and reattach them to the system. There is known a patient monitoring system that can be powered by two power supplies, the patient monitoring system being energized by a battery while the patient wired to the system is being moved from place to place. However, this system is disadvantageous in that it takes up a large space when the patient is moved. When it is desired to replace the system, the electrodes and tranducers have to be detached and reattached. At this time, a blood pressure transducer and other transducers should be re-preset, and patient data items should also be set once more.

SUMMARY OF THE INVENTION

It is an object of the present invention to provide an input device for use with a hard-wire patient monitoring system, the input device being arranged for allowing the patient to be separated from the system and moved and also for allowing the system to be replaced without reconnecting the transducers and resetting the system while the patient is being supervised by the system.

According to the present invention, the above object can be achieved by an input device for a hard-wire patient monitoring system, the input device being composed of a case which can be plugged in the system and from which a plurality of lines for receiving physiological input signals from the patient being monitored, a RAM housed in the case for storing data of the patient necessary for monitoring the patient, a backup battery disposed in the case for backing up the RAM, and a switch housed in the case and actuatable when the case is removed from the system for switching from a system power supply to the backup battery. Signals and power are transmitted between the input device and the system through a plug-in connector. Desired data items are kept in the RAM even when the input device is disconnected from the system.

With the arrangement of the invention, the lines for receiving physiological input signals can be connected to or disconnected from the system in a single action to plug in or out the input device, so that the lines can easily be handled when the patient is separated or moved from the system. Since the patient data items are held in the input device which is shared by replaceable patient monitors, the patient data items are not required to be re-preset and trend data is not eliminated when one system is replaced with another.

The above and other objects, features and advantages of the present invention will become more apparent from the following description when taken in conjunction with the accompanying drawings in which preferred embodiments of the present invention are shown by way of illustrative example.

DESCRIPTION OF THE PREFERRED EMBODIMENTS

Figure 1:
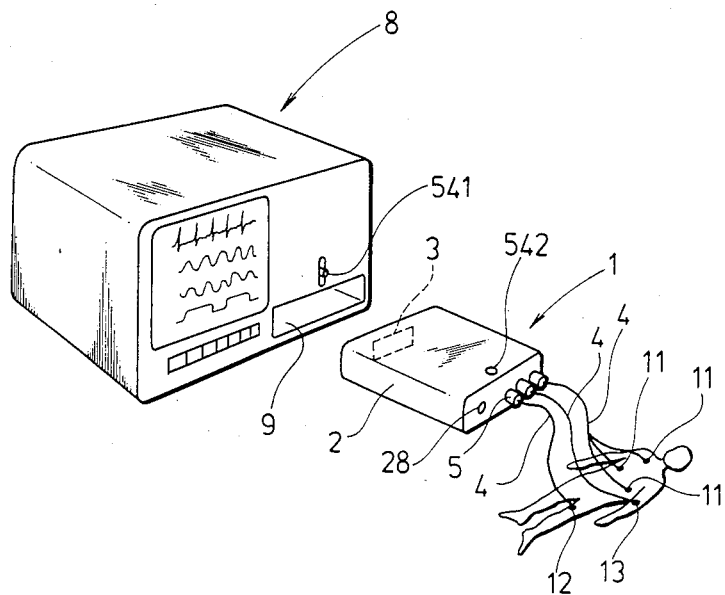
FIG. 1 is a perspective view of an input device for a hard-wire patient monitoring system.
Figure 2:
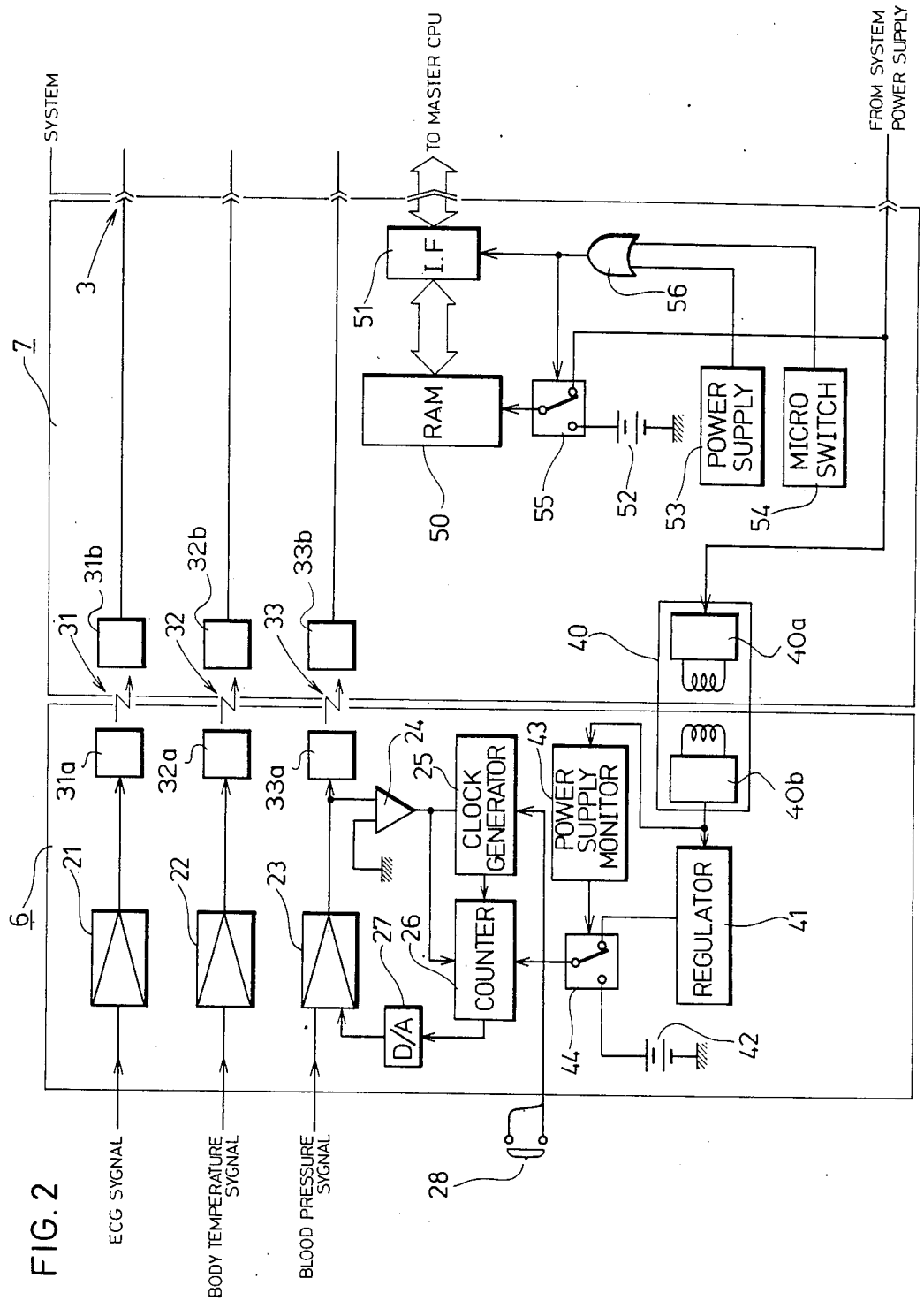
FIG. 2 is a block diagram of the input device.

As shown in FIG. 1, an input device 1 according to the present invention can be plugged into a slot 9 defined in the housing of a patient monitoring system 8. The input device 1 includes a case 2 having a plug-in connector 3 and connector plugs 5 from which there extend lead lines 4 connected to electrodes 11 for detecting electrocardiographic signals, a transducer 12 for detecting a body temperature, and a transducer 13 for detecting a blood pressure. The case 2 accommodates therein a circuit as shown in FIG. 2. The circuit includes a floating section 6 electrically insulated from the system 8 and an interface section 7 coupled by the connector 3 to the system for being supplied with a power supply voltage and transmitting and receiving signals.

The floating section 6 includes an amplifier 21 associated with the electrodes 11 for detecting electrocardiographic signals and an amplifier 22 associated with the transducer 12 for detecting a body temperature. Amplified signals from the amplifiers 21, 22 are supplied to the input elements of isolated transmitters such as optoisolators or photocouplers 31, 32 each being composed of a photo transmitter 31a, 32a and a photo receiver 31b, 32b respectively. The floating section 6 also includes a amplifier 23, a differential amplifier 24 for subtracting the amplified output from the differential amplifier 23 from a reference level, a clock generator 25 for generating clock pulses when the differential output from the differential amplifier 24 is not zero, an up/down counter 26 for counting up the clock signals when the differential output from the differential amplifier 24 is positive and counting down the clock signals when the differential output from the differential amplifier 24 is negative, and a D/A converter 27 for converting the count of the counter 26 into an analog signal. These differential amplifiers 23, 24, the clock generator 25, the up/down counter 26, the D/A converter 27, and a switch 28 mounted on the case 2 for operating the clock generator 25 jointly constitute an amplifier circuit with a zero-balancing capability for amplifying a blood-pressure signal detected by the transducer 13. The blood-pressure signal as amplified by the differential amplifier 23 with the zero level used as a base is supplied via the amplifier circuit to an optoisolator 33 composed of a photo transmitter 33a and a photo receiver 33b. A D/D converter 40 comprises an isolated transmitter in the form of a transformer having its primary winding connected to a DC/AC converter 40a and its secondary winding connected to an AC/DC converter 40b. The floating section 6 also has a regulator 41 for controlling the output voltage from the D/D converter 40 into a constant voltage, a backup battery 42 for backing up the up/down counter 26, and a power supply monitor 43 for monitoring the output voltage from the D/D converter 40 and shifting a switch 44 to the backup battery 42 when the monitored output voltage drops below a prescribed voltage.

The interface section 7 includes a RAM 50 for storing patient data items necessary for monitoring a patient, patient data items including inherent data such as the name, age, sex, height, weight, patient ID, and other data items, data from a monitor for a gas analyzer, etc, time-dependent trend data on electrocardiographic signals and a blood pressure, and other data such as an alarm setting and an ID for a body region where the blood pressure is measured. These patient data items are transmitted and received through an interface 51 between the RAM 50 and a master CPU in the system 8.

Figure 3:
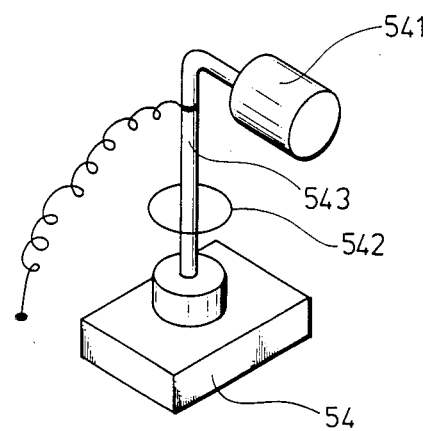
FIG. 3 is a perspective view of a slot-out detector.

The interface section 7 also includes a backup battery 52 for backing up the RAM 50, a power supply monitor 53 for detecting when the a system power supply of the system 8 drops below a prescribed voltage, and a slot-out detector 54 such as a microswitch for detecting when the case 2 is removed from the slot 9. As shown in FIG. 3, a button 541 mounted on the housing of the system 8 for upward sliding movement is normally spring-biased to move downwardly, and a rod 543 is attached to the button 541 and extends downwardly. The microswitch 54 can be pushed downwardly by the lower end of the rod 543 which extends through a hole 542 defined in the case 2. The interface section 7 further includes a switch 55 actuatable by a detected signal supplied from the microswitch 54 or the power supply monitor 53 through an OR gate 56 for switching from the system power supply to the backup battery 52 to keep the RAM 50 energized.

The plug-in connector 3 is coupled to a companion connector (not shown) of the system 8 for transmitting the aforesaid physiological signals, the signals of the RAM 50, and the power of the system power supply between the interface section 7 and the system 8.

When it is desired to monitor a patient, the electrodes 11 and the transducers 12, 13 are attached to the patient. The case 2 is inserted into the slot 9 while the button 541 is manually slid upwardly, and can be locked in place by releasing the button 541 to cause the rod 543 to enter the hole 542, thus turning off the microswitch 54. With the blood pressure transducer 13 set at atmospheric pressure, the switch 28 is depressed in order to set the output level of the differential amplifier 23 to zero. The up/down counter 26 then counts up or down clock pulses from the clock generator 25 dependent on the differential output from the differential amplifier 24. An analog signal from the D/A converter 27 is supplied to the differential amplifier 23 to start a balancing operation. When the differential output from the differential amplifier 23 reaches the zero level, the output from the differential amplifier 24 becomes zero, whereupon no clock pulse is supplied from the clock generator 25 to thereby stop the balancing operation. The count achieved at this time is held as a preset value in the up/down counter 26. The patient inherent data items, and alarm values such as the rate of heart beats and the blood pressure as they are set through the keyboard of the system 8 are stored into the RAM 50 through the CPU in the system 8. The CPU in the system 8 processes the body temperature signal, electrocardiographic signals, and blood pressure signal, as required, supplied from the case 2 to sequentially produce trend data items for display, and stores these trend data items, together with data items from other monitors, into the RAM 50. A cardiac output and other data items are computed by the CPU in the system 8 on the basis of the inherent data items stored in the RAM 50 and then are stored back in the RAM 50. The system 8 has a display for displaying selected data items read from the RAM 50 in a selected display mode.

If the system power supply fails momentarily or for a certain time, then the power supply monitors 40, 53 detect the system power supply failure and shift the switches 44, 55, respectively, to the backup batteries 42, 52 to thereby prevent the stored data items from being erased from the up/down counter 26 and the RAM 50. When it is desired to separate the system 8 from the patient at the time of moving the patient or replacing the system, the button 541 is manually slid upwardly and the case 2 is pulled out of the slot 9 without disconnecting the connectors 5 coupled to the electrodes 11 and the transducers 12, 13. Since the microswitch 54 is released and hence turned on to generate a slot-out signal for shifting the switch 55 before the system power supply is subject to chattering. Therefore, the RAM 50 is backed up against data erasure. At the same time, the input and output sides of the interface 51 are separated from each other to hold the data items reliably in the RAM 50 without disturbance. The power supply monitor 43 detects the droppage of the output voltage of the D/D converter 40 due to the system power supply failure for thereby shifting the switch 44. Any adverse effect of the chattering of the system power supply on the output voltage of the D/D converter 40 is filtered out by the capacitance present in the D/D converter 40. When the patent is to be connected to the system 8 again, the button 541 is lifted and the case 2 is inserted into the slot 9 to connect the lines to the system 8. Since the up/down counter 26 is backed up by the backup battery 42, it is not necessary to preset the blood pressure measuring circuit. When the system 8 is to be replaced, the inherent data items and trend data items are not required to be set again and not lost as they are held in the RAM 50.

Figure 4:
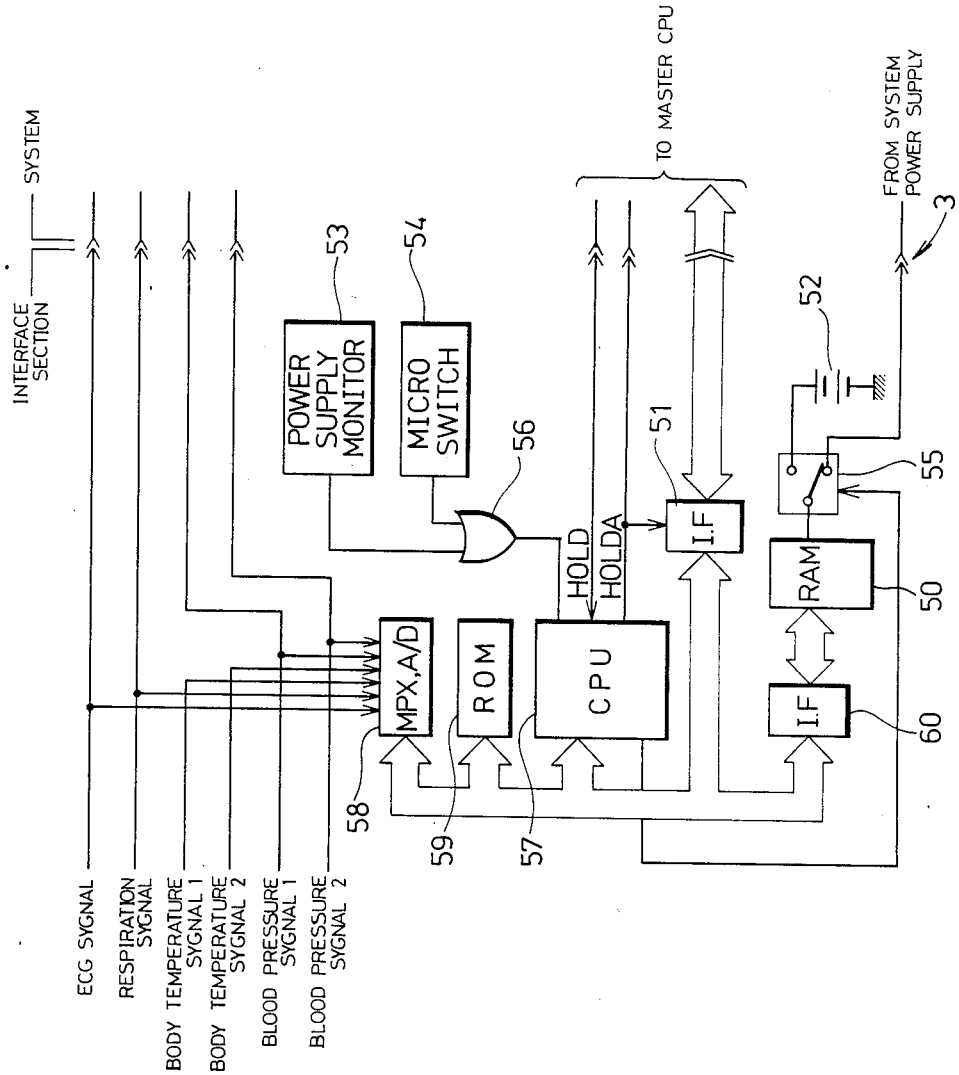
FIG. 4 is a block diagram of an input device according to another embodiment of the present invention.

FIG. 4 illustrates an input device according to another embodiment of the present invention. The input device of FIG. 4 is associated with additional transducers, i.e., a transducer for detecting a body temperature of another body region, a transducer for detecting respiration, and a transducer for detecting a blood pressure of another body region. Therefore, the floating section 6 of the input device 1 additionally includes an amplifier, a presettable amplifier, and an isolated transmitter (not shown), a CPU 54 for processing patient data items in a primary mode, a multiplexer-A/D converter 58 for successively selecting physiologinal signals and converting them to analog signals, a ROM 59 for storing the program to operate the CPU 57, and an interface 60 for signal transmission between the CPU 57 and the RAM 50. The CPU 57 generates the trend data items and stores them into the RAM 50, and monitors the output from the OR gate 56 to shift the switch 55. The master CPU in the system 8 only displays the primary data items generated by the CPU 57, effects data communication, and processes secondary data items. To effect the above processing, the master CPU successively delivers HOLD signals to the CPU 57. When a HOLDA signal is sent back from the CPU 57 to the master CPU in response to the HOLD signal, the master CPU fetches the data items from the RAM 50 through the interface 51. Therefore, the patient data items are generated by the input device 1 itself, and the master CPU is freed from the primary processing which requires repetitive real-time processing, but can effect higher-level processing.

The slot-out detection can be achieved also by passing the system power through a low-pass filter so that it is free from the chattering and by detecting the system power through the filter. With this arrangement, the microswitch 54 may be dispensed with. In FIGS. 1 and 2, the optoisolators 31 through 33 may be disposed in the system 8, and the output terminals of the connectors 5 may be directly coupled to the plug-in connector 3 whereas only the circuitry for holding the patient data items and preset values may be disposed in the case 2.

Although certain preferred embodiments have been shown and described, it should be understood that many changes and modifications may be made therein without departing from the scope of the appended claims.

What is claimed is:

1. An input device for use in a hard-wire patient monitoring system, comprising:

a case having a plug-in connector for plug-in connection to a patient monitoring system and a plurality of lines for receiving physiological input signals to be supplied to said patient monitoring system through said plug-in connector for processing said physiological input signals;

a memory storage device disposed in said case, and connected to said plug-in connector for storing and reading out patient data items necessary for monitoring a patient;

a backup battery power source disposed in said case and connected to said memory storage device for energizing said memory storage device when said case is disconnected from said patient monitoring system;

a switch disposed in said case for switching from a power supply of said patient monitoring system to said backup battery power source to maintain said memory storage device energized; and means interconnected with said switch and said backup battery power source for actuating said switch in response to detachment of said case from said patient monitoring system.

2. An input device according to claim 1, including a circuit arrangement disposed in said case and composed of a floating circuit section isolated from the patient monitoring system, an interface circuit section not isolated from the patient monitoring system and isolated transmitters connected between said floating and interface circuit sections, said floating circuit section including amplifiers for amplifying the physiological signals supplied from said lines, said interface circuit section including said memory storage device, said isolated transmitters having input elements supplied respectively with amplified signals from said amplifiers.

3. An input device according to claim 2, including means disposed in said floating circuit section for holding a preset value for a physiological blood pressure signal measuring circuit.

* * * * *